(12) United States Patent  (10) Patent No.: US 8,167,864 B2
Browne  (45) Date of Patent: May 1, 2012

(54) SPIKE-ACCOMMODATING CONTAINER HOLDER

(75) Inventor: Martin Browne, Oslo (NO)

(73) Assignee: GE Healthcare AS, Oslo (NO)

( * ) Notice: Subject to any disclaimer, the term of this patent is extended or adjusted under 35 U.S.C. 154(b) by 483 days.

(21) Appl. No.: 12/096,030

(22) PCT Filed: Dec. 12, 2006

(86) PCT No.: PCT/NO2006/000477
§ 371 (c)(1),
(2), (4) Date: Jun. 4, 2008

(87) PCT Pub. No.: WO2007/069907
PCT Pub. Date: Jun. 21, 2007

(65) Prior Publication Data
US 2009/0005753 A1   Jan. 1, 2009

(51) Int. Cl.
*A61B 19/00* (2006.01)
*A61M 5/32* (2006.01)
(52) U.S. Cl. .................. 604/414; 604/403; 604/411
(58) Field of Classification Search ........... 604/403–416
See application file for complete search history.

(56) References Cited

U.S. PATENT DOCUMENTS

| | | | |
|---|---|---|---|
| 5,458,567 A * | 10/1995 | Cathcart | 604/6.15 |
| 5,472,434 A | 12/1995 | Lechleiter | |
| 5,769,138 A | 6/1998 | Sadowski et al. | |
| 5,934,510 A | 8/1999 | Anderson | |
| 5,989,237 A * | 11/1999 | Fowles et al. | 604/413 |
| 6,364,170 B1 | 4/2002 | Anderson | |
| 6,439,276 B1 * | 8/2002 | Wood et al. | 141/97 |
| 2003/0199847 A1 | 10/2003 | Akerlund et al. | |
| 2004/0210192 A1 | 10/2004 | Degentesh et al. | |

FOREIGN PATENT DOCUMENTS

| | | |
|---|---|---|
| DE | 102005006771 | 8/2006 |
| EP | 0367549 | 5/1990 |
| WO | 86/01712 | 3/1986 |

OTHER PUBLICATIONS

PCT/NO2006/000477 ISR-WO Dated Apr. 2007.

* cited by examiner

*Primary Examiner* — Tatyana Zalukaeva
*Assistant Examiner* — Philip R Wiest
(74) *Attorney, Agent, or Firm* — Robert F. Chisholm

(57) ABSTRACT

A holding device for a container having a closure system to be pierced by a spike includes a base, a shield, and a mounting unit supporting the base. The base includes an elongate body having opposed first and second ends and an elongate body extending therebetween. The base body defines an elongate open spike cavity extending between opposing ends thereof. The channel receives an elongate spike therein so that a free end of the spike extends beyond the base body from the channel. The shield includes first and second opposed open ends and an elongate cylindrical wall extending therebetween. The shield is telescopically mounted over the base so as to be movable between a first position wherein an inserted spike is clear of inserted container cap and a second position wherein the spike pierces through the septum of the container cap at the intended location.

19 Claims, 17 Drawing Sheets

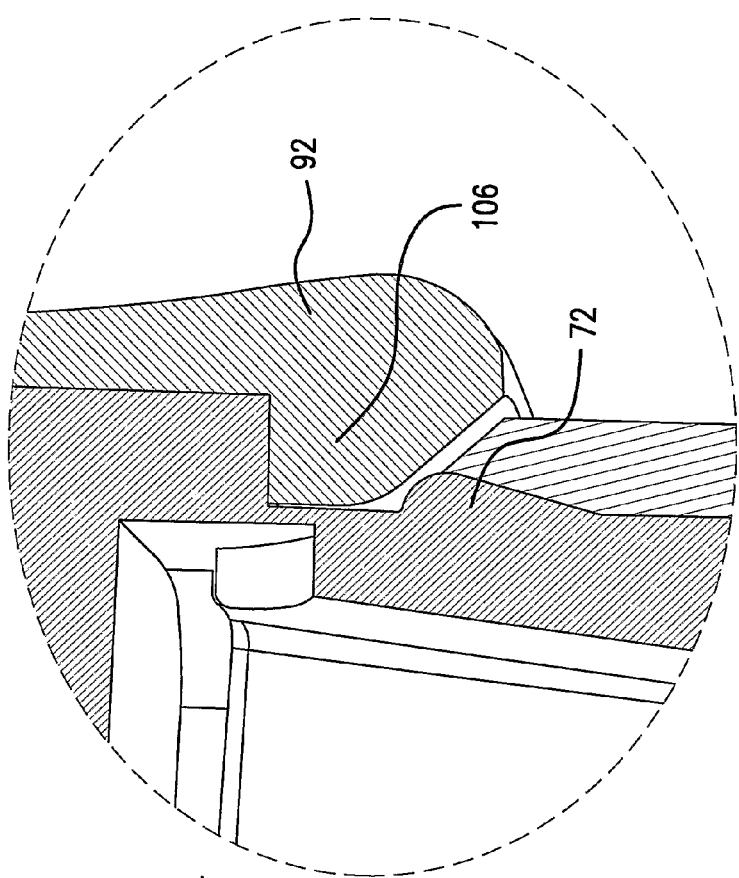
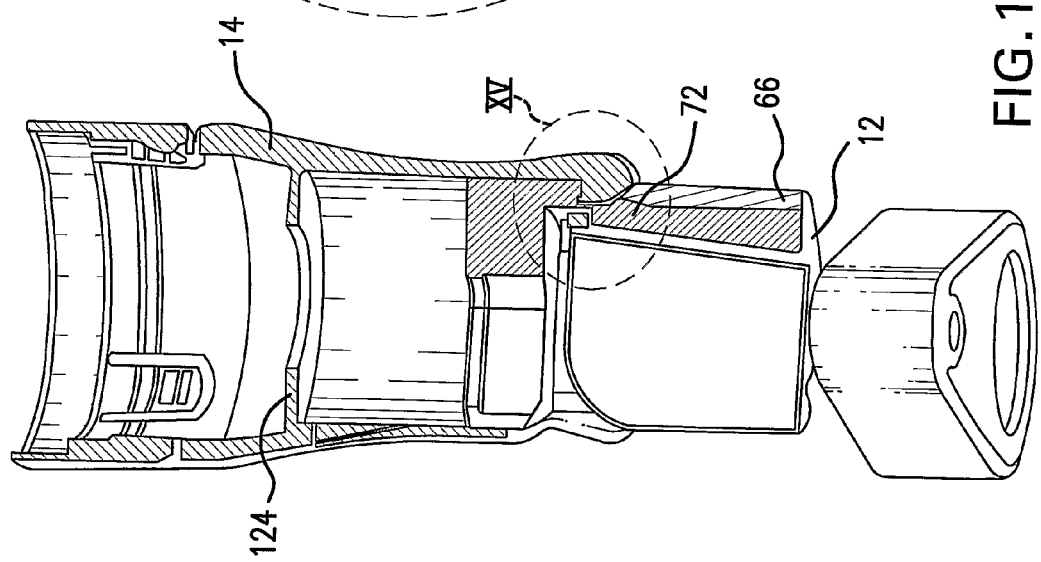
FIG. 15
FIG. 14

SPIKE-ACCOMMODATING CONTAINER HOLDER

FIELD OF THE INVENTION

The present invention is directed to the field of container holders. More specifically, the present invention is directed to a combination holder for both a spike and a container.

BACKGROUND OF THE INVENTION

When using a container of a pharmaceutical to be provided intravenously, the art has seen different methods for securing that container while the pharmaceutical is dispensed or removed therefrom. For example, some bag containers include an eyelet or hangar hook by which the container may be suspended. The contents of the container may be withdrawn by a powered injector which draws the contents from the container for injection into a patient. Powered injectors may be used for multi-dosing of a contrast media and may provide both automated saline flushing and purging of the fluid conduits. Efficiency may be increased by the use of powered injectors as set-up can be relatively quick and very little contrast media is wasted between patients.

Alternatively, when the container is a plastic or glass bottle, a label affixed to the container may include a pre-cut portion not affixed to the container so as to be able to deflect away from the container and provide a loop by which the container may be hung. U.S. Pat. No. 5,135,125 provides an example of a hangar label used to hang the container to which it is attached. The container typically includes a cap supporting a spike-pierceable septum, or closure, which, when the container is hung, faces the floor. The spike is inserted so as to project upward into the container as it hangs. Such containers provide a cheaper alternative to more expensive contrast media cartridges which provide a large syringe-like body with an internal piston for dispensing the contents.

However, hanging containers also have several drawbacks. The hook on which the container hangs must in some cases be adjusted for each container. The spike which pierces the container's septum has a fixed height and may be inadvertently extended so far into the container that a large pool of product will collect between the spike tip and the top of the septum, causing that amount of product to go to waste. Improper setting of the hook may render the container unstable or otherwise improperly supported. Additionally, since the bottle and the spike typically tilts during use, and also because of the difficulty to properly center the spike when piercing the septum, there is the potential for leaks.

There is therefore a need in the art for a bottle holder that can increase efficiency by reducing the time to arrange the bottle while still properly centering the spike through the septum. The holder should reduce the potential for wasted or unused contrast media by optimally positioning the spike at the lowest drain point in the bottle cap just inside the septum. Additionally, the holder should provide a cap opener for allowing easy removal of a protective tab on the container cap so as to expose the septum. Moreover, when the spike is provided with an openable vent, the holder should selectively provide for the opening of that vent.

SUMMARY OF THE INVENTION

In view of the needs of the art, the present invention provides a holding device for a container having a closure system to be pierced by a spike. The holder includes a base, a shield, and a mounting unit supporting the base. The base includes an elongate body having opposed first and second ends and an elongate body extending therebetween. The base body defines an elongate open channel extending between opposing ends thereof. The channel receives an elongate spike therein so that a free end of the spike extends beyond the body from the channel. The shield includes first and second opposed open ends and an elongate cylindrical wall extending therebetween. The container receiving unit is telescopically mounted over the spike receiving unit so as to be movable between a first position wherein an inserted spike is clear of inserted container cap and a second position wherein the spike pierces through the container closure system at the intended location.

BRIEF DESCRIPTION OF THE DRAWINGS

FIGS. 14 and 15 are cross-sectional views detailing the engagement between the shield and the base when the shield is in the raised, or extended, position.

DETAILED DESCRIPTION OF THE PREFERRED EMBODIMENT

Figure 1:
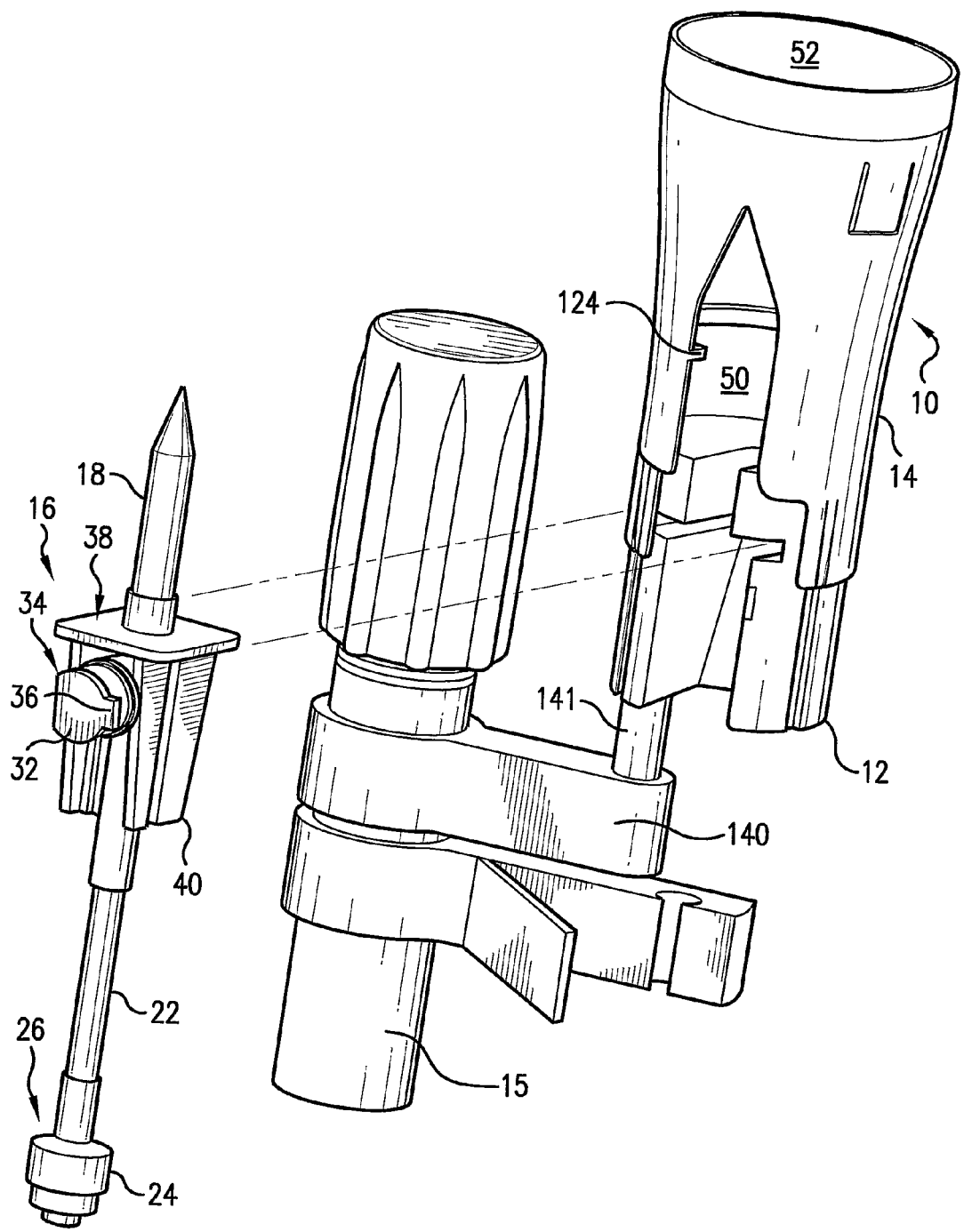
FIG. 1 depicts the base and the shield of a bottle holder of the present invention with spike to be received therein.
Figure 2:
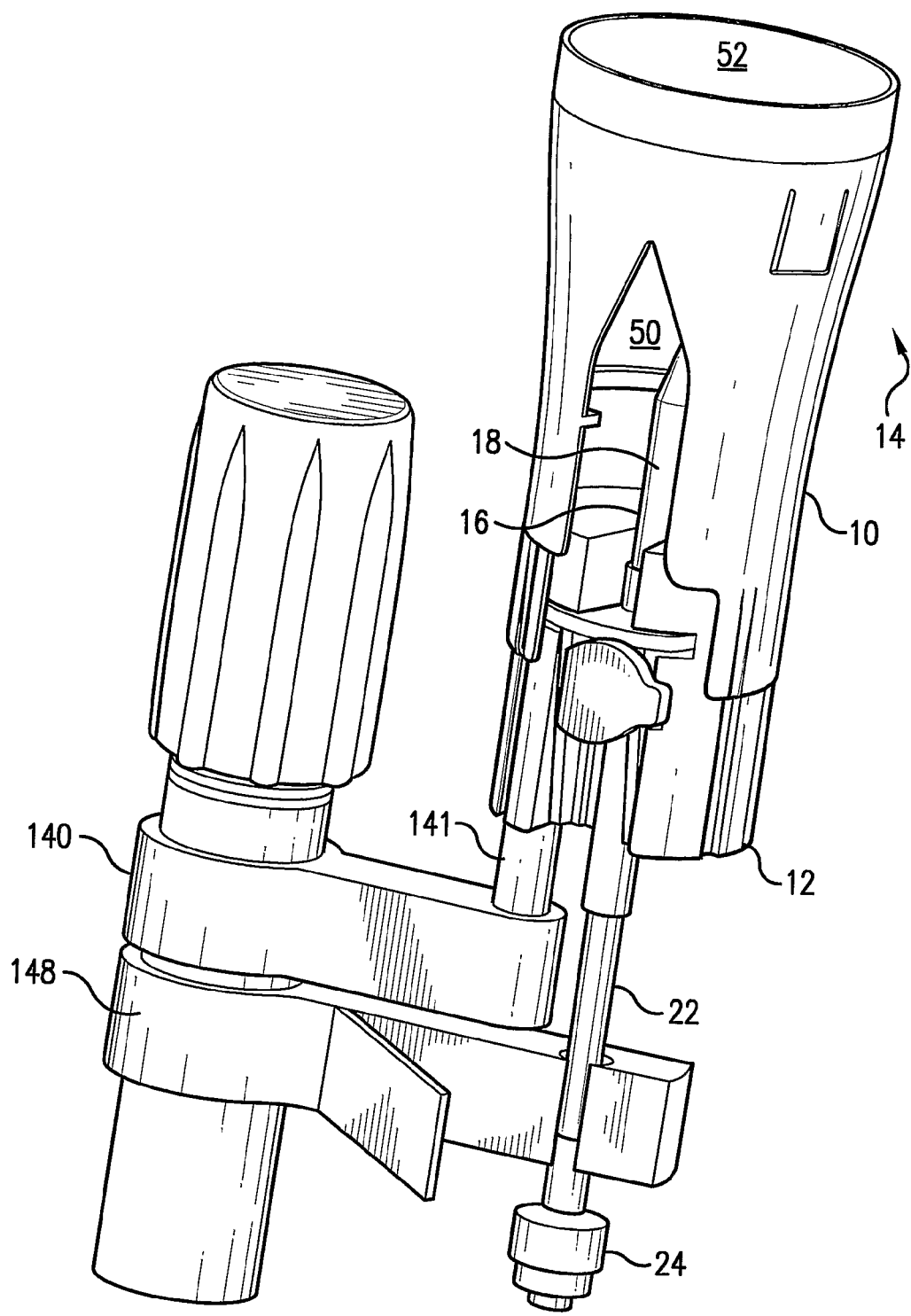
FIG. 2 depicts the bottle holder of FIG. 1 with the Luer-type spike inserted into the spike receptacle thereof.
Figure 3:
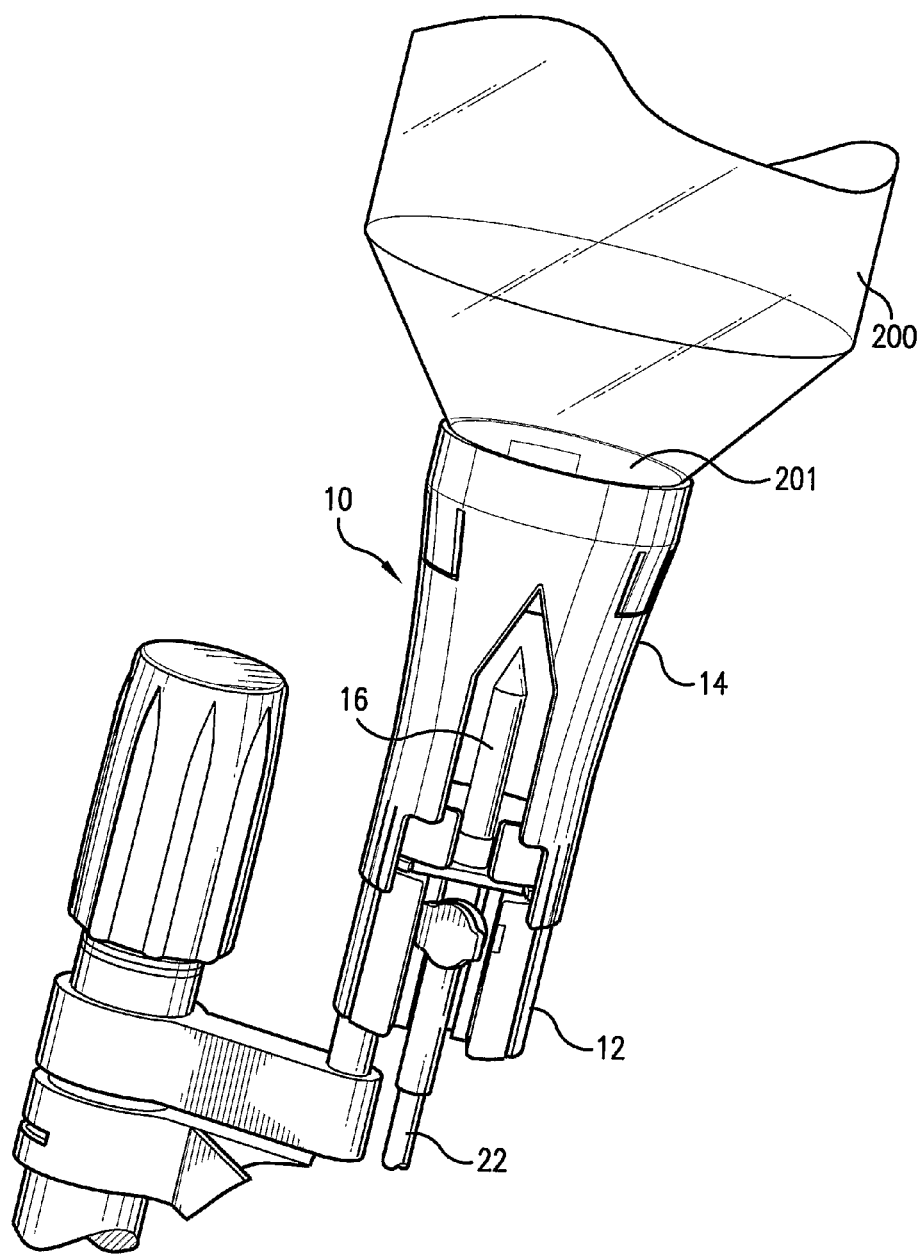
FIG. 3 depicts the assembly of FIG. 2 in which the cap of a container has been mated to the bottle receptacle of the shield so that the septum of the container cap is centered over the Luer-type spike.
Figure 4:
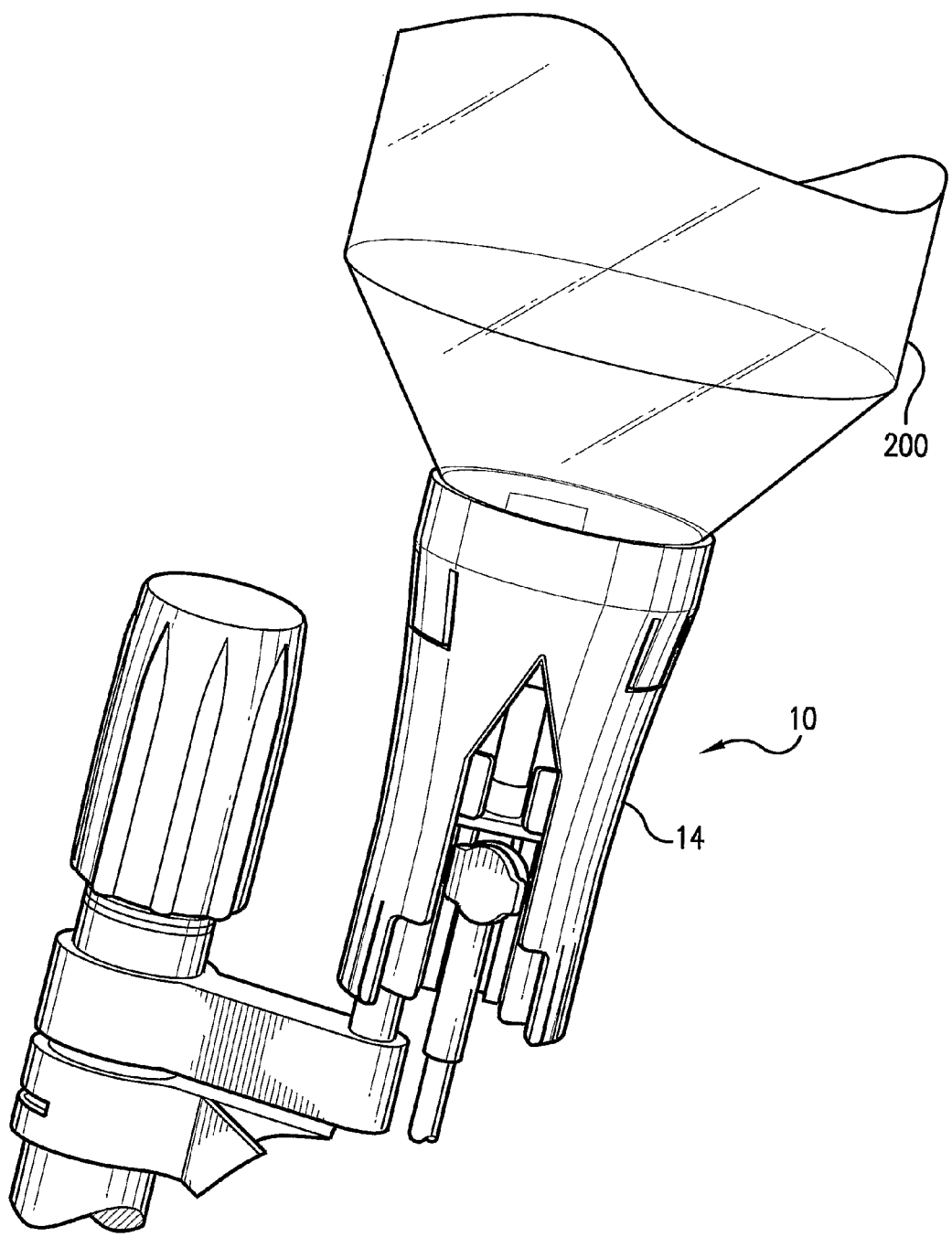
FIG. 4 depicts the assembly of FIG. 2 in which the shield has been retracted towards the base so that the Luer-type spike has penetrated the septum of the container cap.

FIGS. 1-5 and 11 depict a bottle holder 10 of the present invention. Bottle holder 10 includes a base 12 and a shield 14 which can slide thereover between a first extended position and a second retracted position. The base and the shield are desirably formed from suitable polymeric material although any suitable material may be used for their construction. Bottle holder 10 is designed to be mounted to an upright pole 15, such as an ACIST™ bottle stand, so as to have a vertical orientation as shown in FIG. 1. Holder 10 defines a transversely-opening spike-receptacle 50 and an axially-opening bottle receptacle 52 in fluid communication therewith. When shield 14 is in the extended position, as shown in FIG. 1, a spike 16 may be inserted into bottle holder 10.

Figure 5:
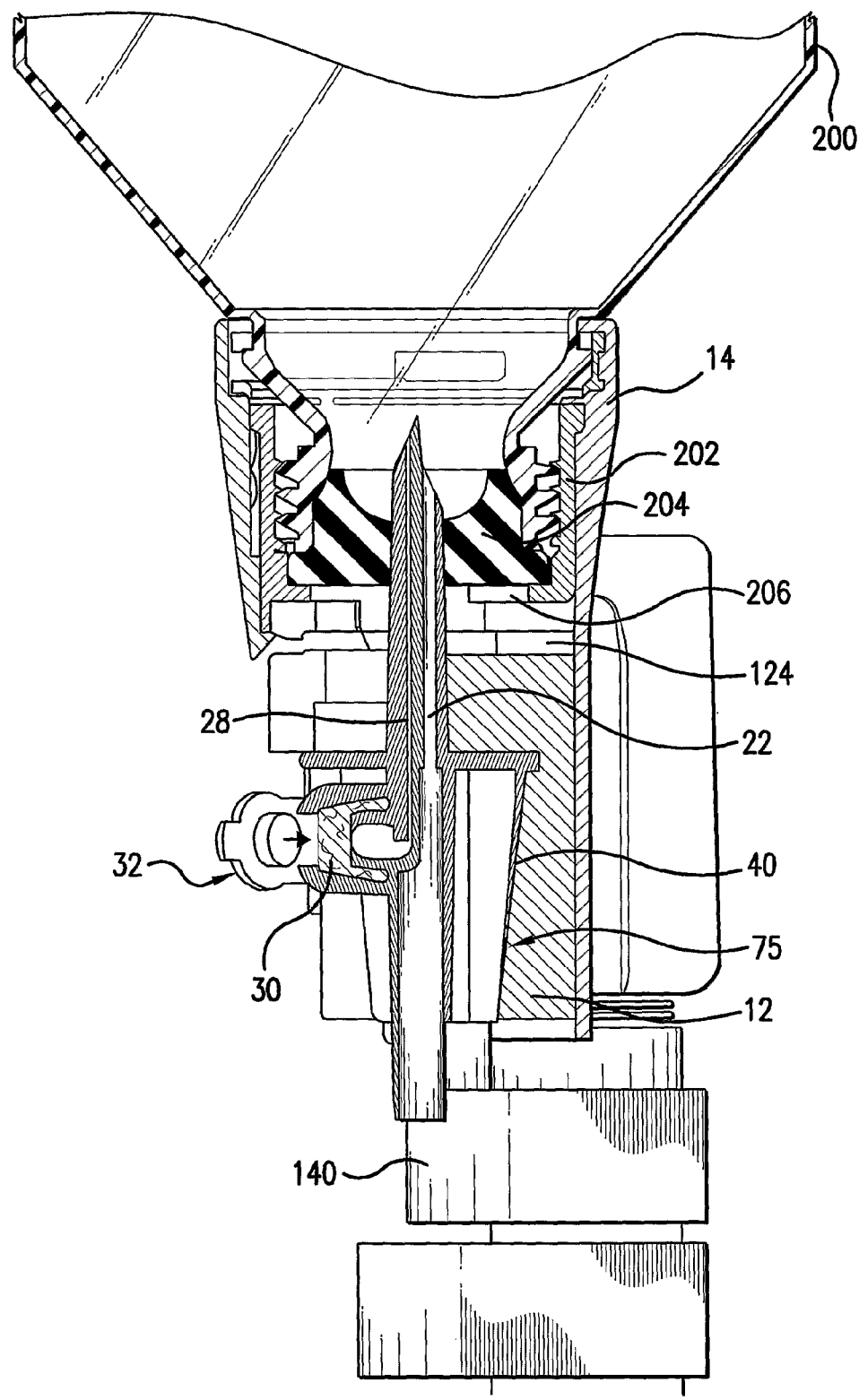
FIG. 5 is a cross-sectional view of the assembly of FIG. 4, showing the penetration of the spike through the septum of the container cap.

With particular reference to FIGS. 1 and 5, spike 16 typically includes an elongate dual-lumen spike body 18 with a first lumen 20 in fluid communication with an elongate hollow fluid conduit 22 supporting a luer lock 24 at a free end 26 thereof. Spike 16 also typically includes and a second lumen 28 in fluid communication with a spike vent 30 sealable by an openable vent plug 32 flexibly supported at a hinge 34 affixed to spike body 18. Vent plug 32 includes a projection 36 extending in opposition to hinge 34. Spike 16 further includes a planar spike base 38 and tapering rectangular supporting base structure 40.

Referring now to FIGS. 5, 11 and 17-19, bottle 200 includes an open end 201 supporting a cap 202 over a pierceable elastomeric septum 204. Cap 202 defines an aperture 206 through which spike body 18 may extend to pierce septum 204. Bottle 200 may further include a foil extending across the top surface of septum 204. Cap 202 further includes an exterior rim 210 which may support an annular flange or protrusion 212. Bottle 200 is typically formed of plastic or glass and contains a liquid to be dispensed, such as a pharmaceutical compound containing a medical contrast agent.

While the holder of the present invention may be used for accommodating a +PLUSPAK™ container marketed by Amersham Health AS, it will be appreciated that the teachings of the present invention may be applied to accommodate a wide variety of rigid containers having a cap with a pierceable septum. Additionally, while holder 10 is mountable to an ACIST™ bottle stand it will be appreciated that the present invention contemplates that holder 10 may be adapted for mounting upon a variety of structures.

Figure 17:
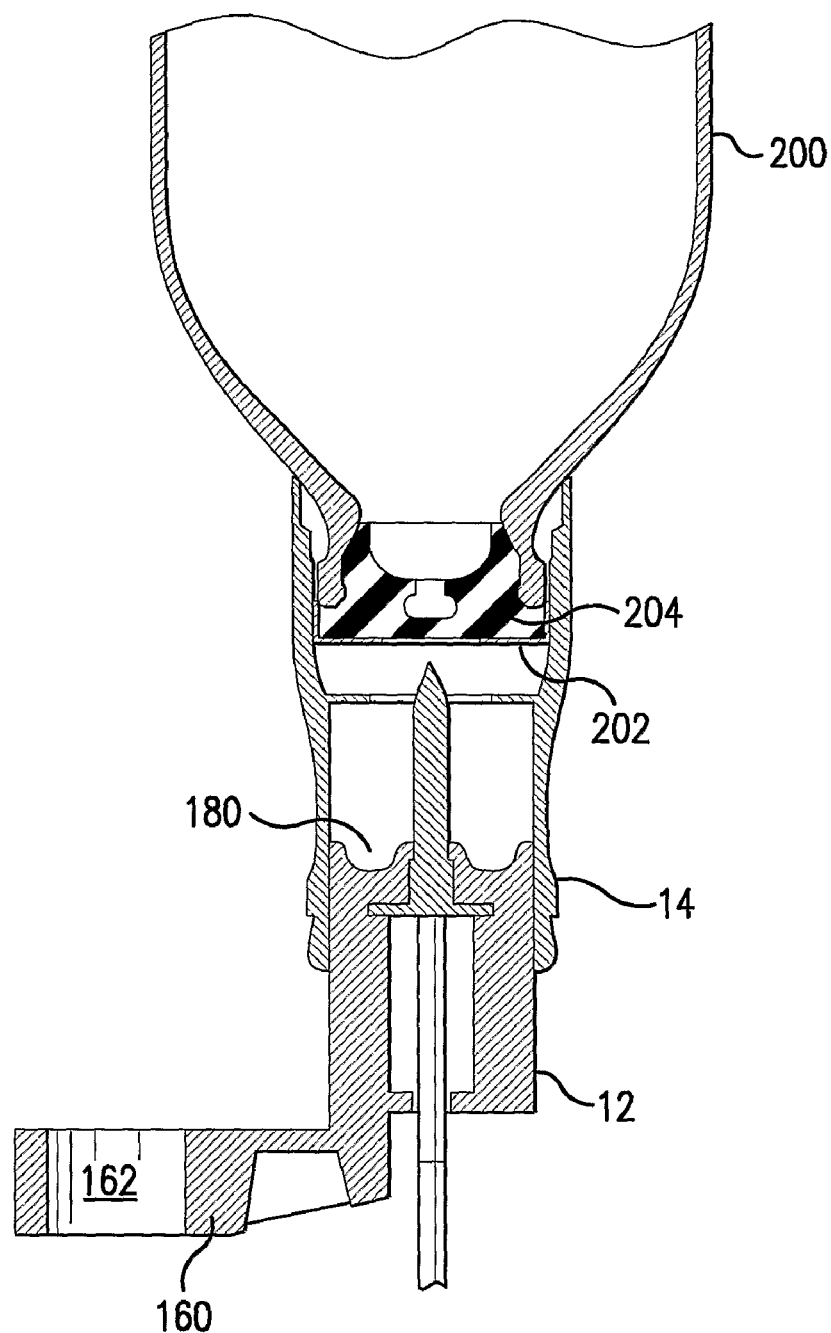
FIG. 17 is a cross-sectional view of a spike and bottle attached to the holder of the present invention, showing the shield in the extended position.
Figure 18:
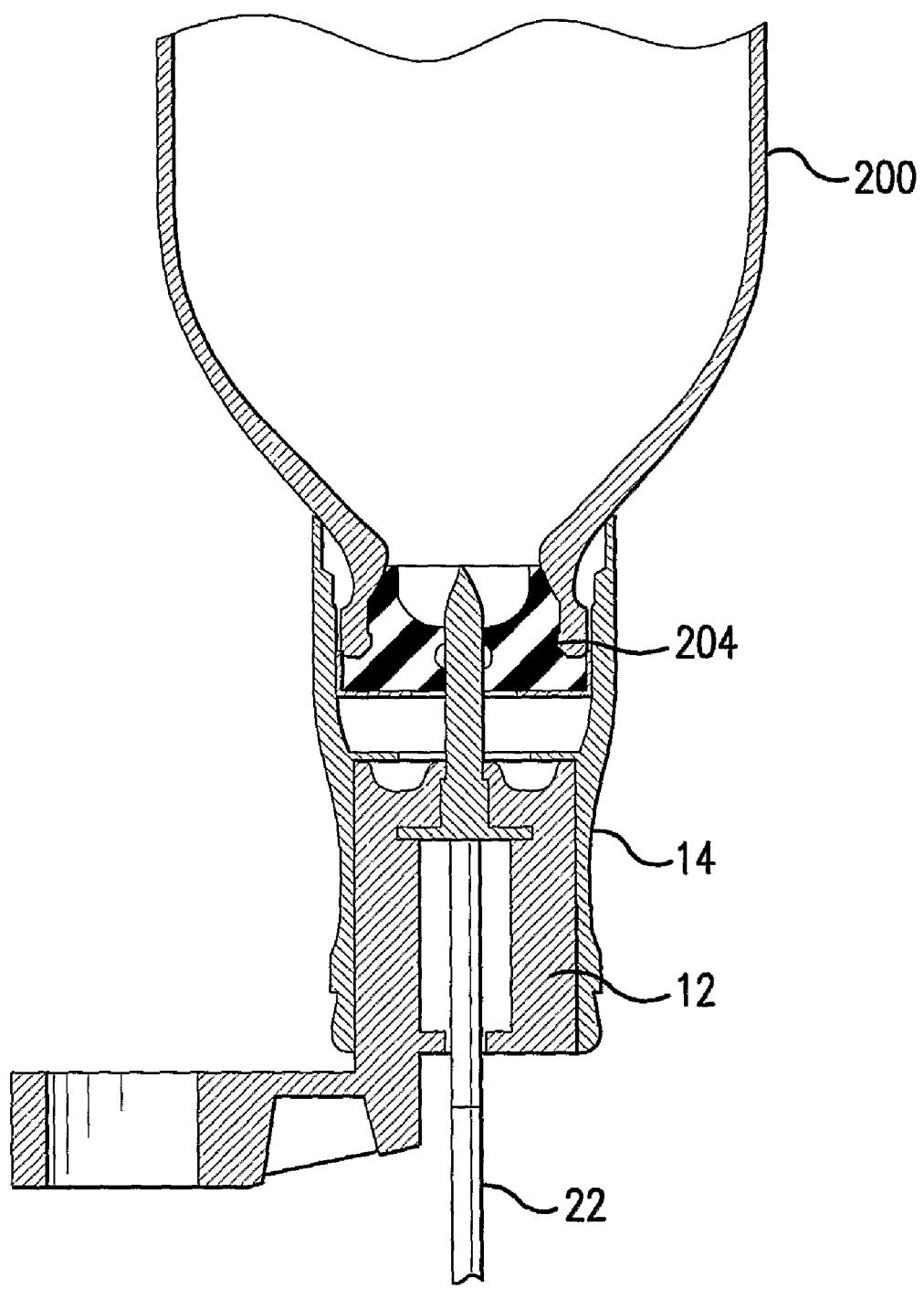
FIG. 18 is a cross-sectional view of a spike and bottle attached to the holder of the present invention, showing the shield in the retracted, or lowered, position, such that the spike pierces the septum of the bottle.

Referring again to FIGS. 1-5, and with additional reference to FIGS. 17 and 18, after spike 16 is properly inserted into spike receptacle 50, spike body 18 extends out from base 12 towards receptacle 52. A bottle 200 may be brought down so that cap 202 is inserted into bottle receptacle 52. Shield 14 engages cap 202 such that as bottle 200 is further brought down, shield 14 slides over base 12 and spike body 18 penetrates through septum 204. The two lumens 20 and 28 will be in fluid communication with the interior of bottle 200. Preferably, vent plug 32 is in the open position so as to assist the flow of liquid product through conduit 22. In operation, a second fluid conduit, not shown, has been connected at luer lock 24 to place the contents of bottle 24 in fluid communication with the vasculature of a patient or animal.

Figure 6:
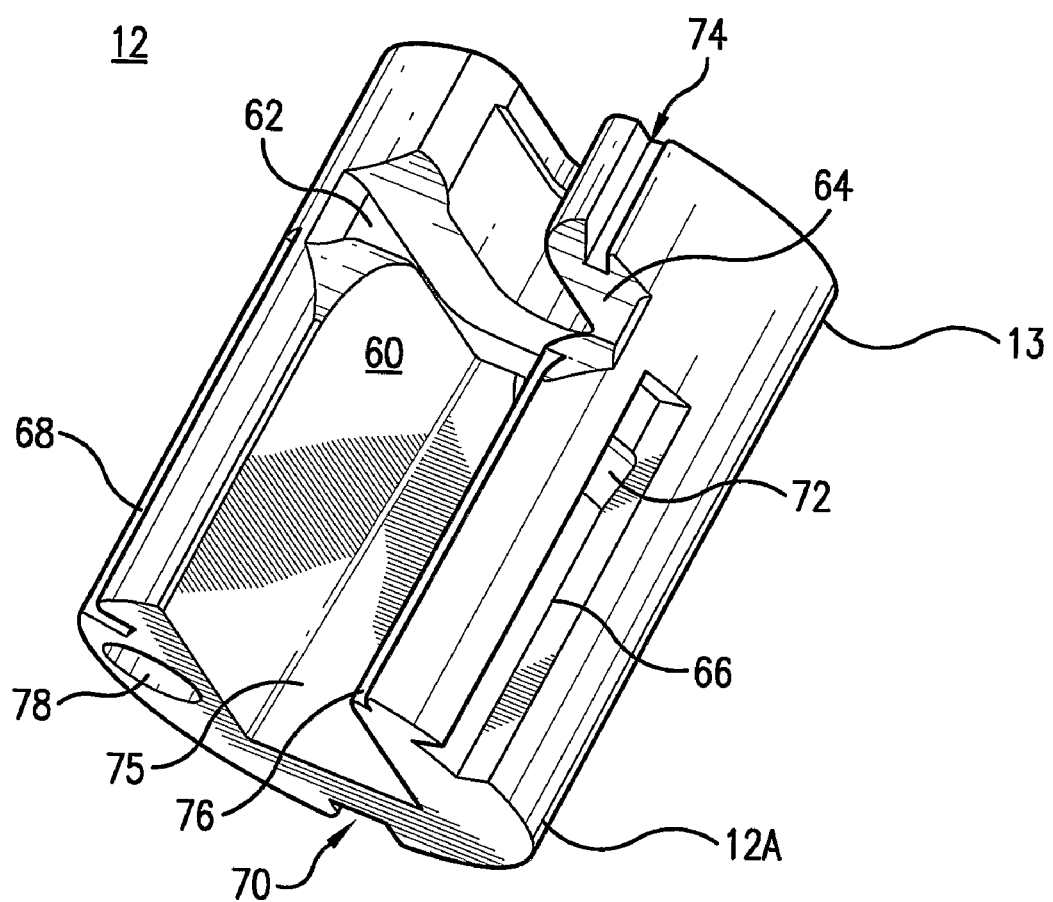
FIG. 6 is an oblique view of a base of the present invention.
Figure 9:
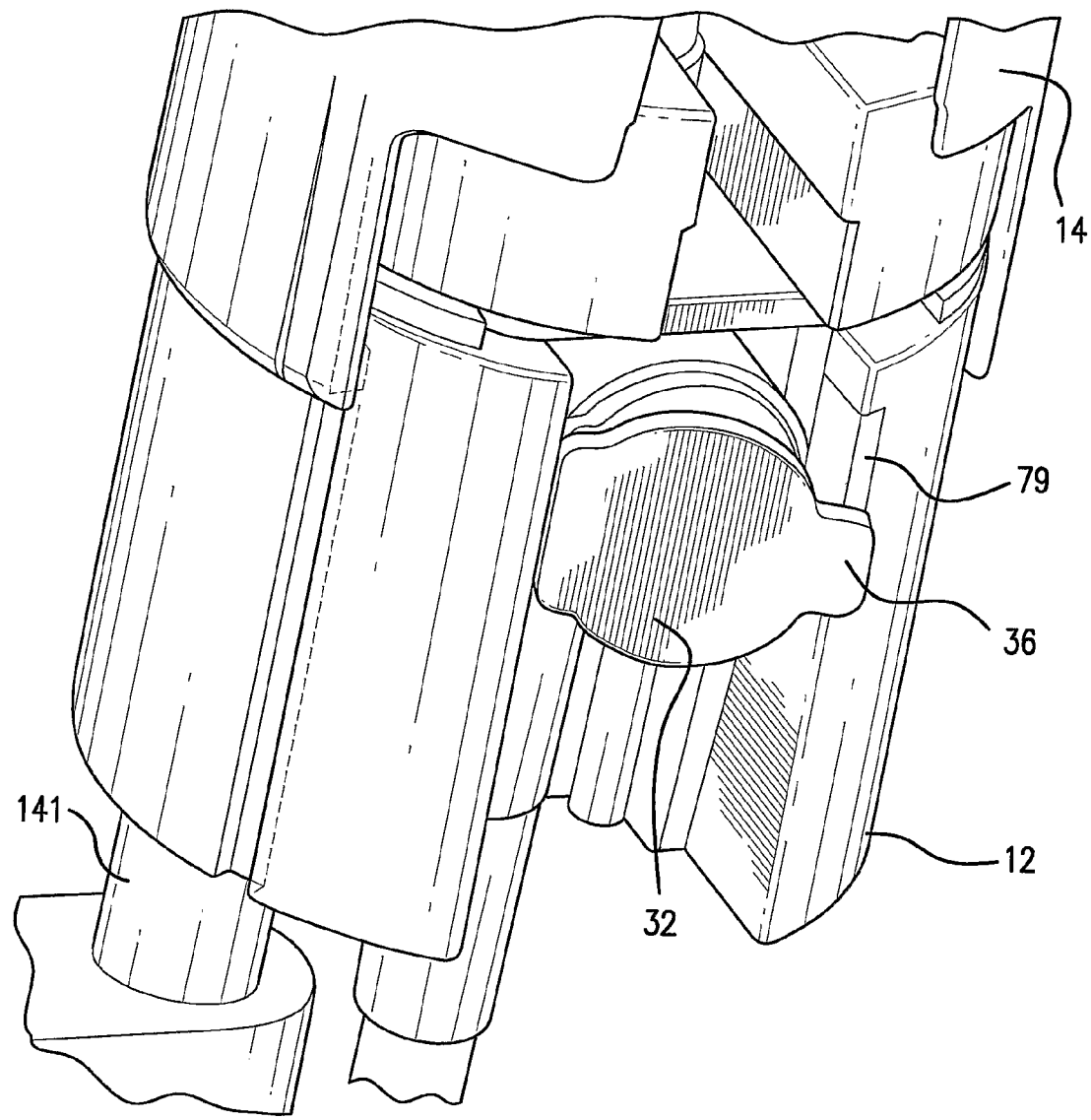
FIG. 9 is a partial view of a bottle holder of the present invention having a tab for opening the vent of the spike upon spike insertion into the spike receptacle.

As shown in FIG. 6, base 12 is shown to include a generally cylindrical body 13 and defines an elongate transversely-opening spike cavity 60 which forms a portion of spike receptacle 50. Spike cavity 60 includes a pair of lateral notches 62 and 64 opening in facing opposition to each other. Notches 62 and 64 receive the lateral extremities of planar spike base 38 therein. Base 12 desirably includes one or more detents or projections, not shown, extending into notches 62 and 64 for base 38 to be inserted over so as to assist in retaining spike 16 within cavity 60. Base 12 also defines three outwardly-opening elongate grooves 66, 68, and 70 extending from the lower end 12a thereof. Each of grooves 66, 68, and 70 support a detent 72 adjacent their upper end (towards shield 14). It is further contemplated that base 12 may also define two slots, an elongate outwardly-opening first slot 74 extending in spaced registry with a second slot 76, as will be described later. Alternatively, as shown in FIG. 9, base 12 may be provided with an insert tab 79. The exposed end of insert tab 79 is positioned in interfering registry with projection 36 on the displaceable cover 32 of spike 16. If insert tab 79 is present it automatically opens spike vent 32 when spike 16 is inserted into cavity 60. Desirably, insert tab 79 is removable such that, when removed, spike vent 32 must be manually opened (and can also be closed) by the radiology technologist. As shown in FIGS. 5 and 6, base 12 desirably further includes a tapered, i.e. sloping, back wall 75 which is angled to conform to the shape of base structure 40 of spike 16.

Referring again to FIG. 6, base 12 may further define an aperture 78 for receiving a mounting pin 141. Mounting pin 141 protrudes from mounting bar 140 which is fixed to pole 15 as shown. e.g., in FIG. 1.

Figure 7:
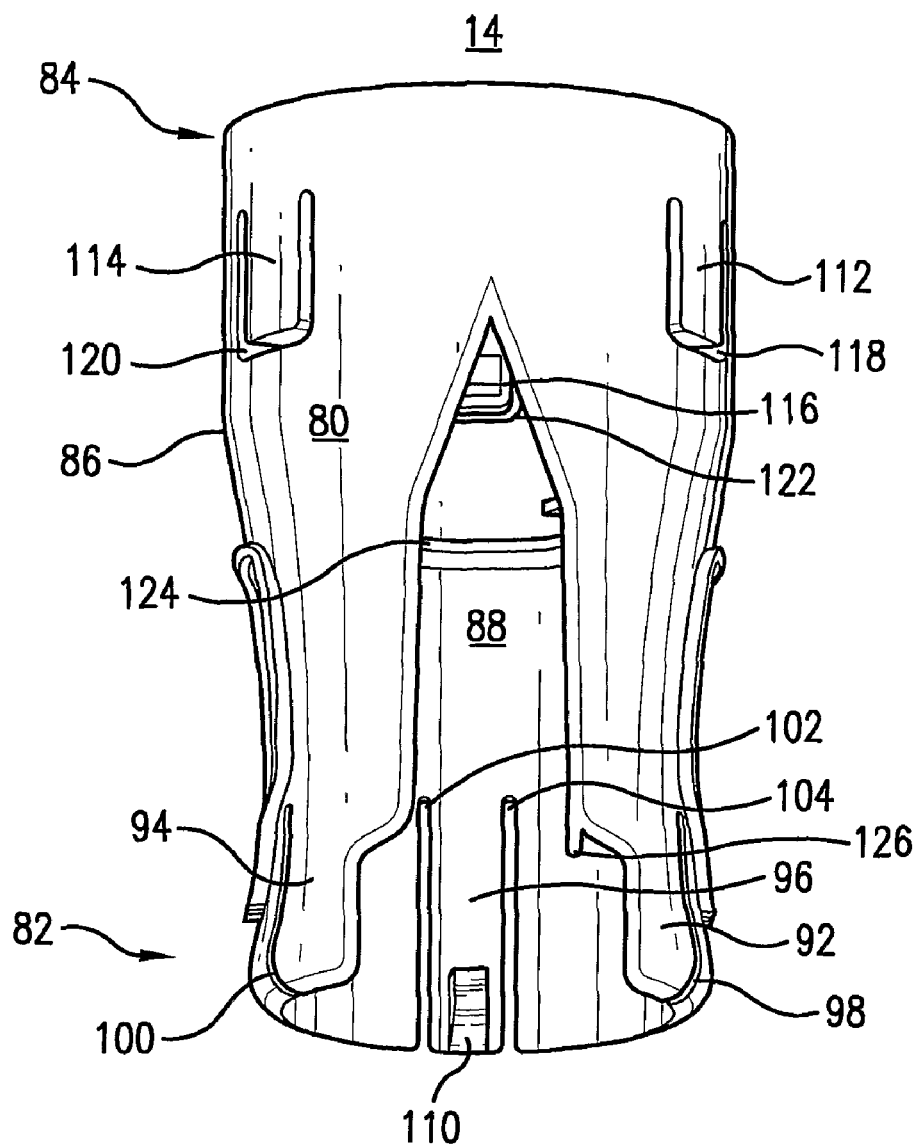
FIG. 7 is an oblique view of a shield of the present invention.
Figure 8:
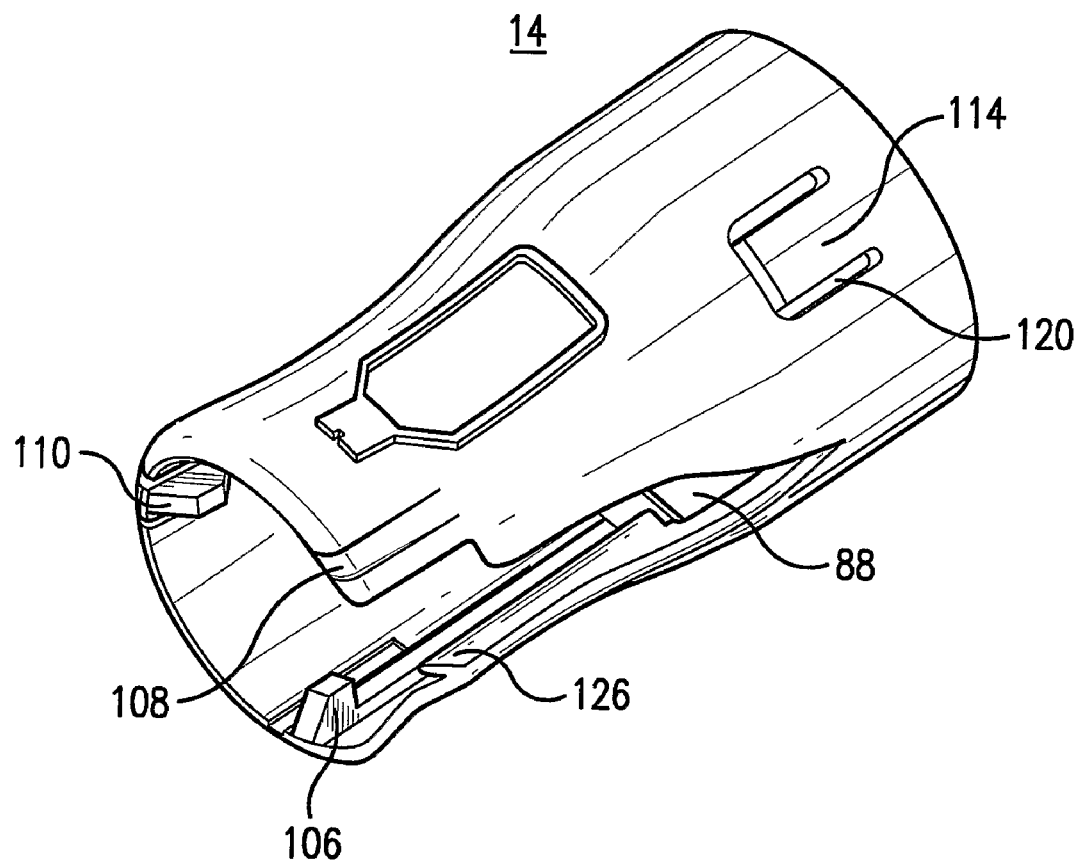
FIG. 8 is an alternate oblique view of a shield of the present invention.

FIGS. 7 and 8 show that shield 14 includes an elongate shield body 80 with first open end 82, second open end 84 and an elongate cylindrical frustroconical wall 86 extending therebetween. End 82 of shield 14 is slideably receivable over base 12. Shield body 80 defines an elongate transversely-opening spike cavity 88 which forms a portion of spike receptacle 50. Cavity 88 is in fluid communication with cavity 60 of base 12, which together form spike receptacle 50. End 84 of shield 14 defines bottle receptacle 52 (see FIG. 1) which is also in fluid communication with cavity 88. End 82 of shield body 80 includes deflectable tabs 92, 94 and 96. Tabs 92 and 94 are defined between spike opening 88 and elongate grooves 98 and 100, respectively. Tab 96 is formed between two elongate channels 102 and 104 opposite spike cavity 88. Tabs 92, 94, and 96 each support a tooth 106, 108, 110, respectively, adjacent to the free ends thereof.

End 84 of shield 14 is designed for receiving and retaining the cap 202 of a bottle 200. Shield 14 includes deflectable bottle detents 112, 114, 116 defined by a block-U-shaped channels 118, 120, 122, respectively. Shield 14 also includes an inwardly-projecting annular rim 124 extending along the interior surface of wall 86. As seen in FIG. 5, rim 124 provides a hard stop for the movement of shield 14 along base 12. Rim 124 desirably is located so as to ensure the tip of spike 16 just penetrates septum 204 enough so as to render both fluid paths 22 and 30 in fluid communication with the interior of bottle 200. Such positioning of spike 16 through septum 204 ensures that spike 16 is able to withdraw the maximum amount of fluid from bottle 200 as fluid path 30 is desirably located just above the interior surface of septum 204 in the inverted position.

Figure 13:
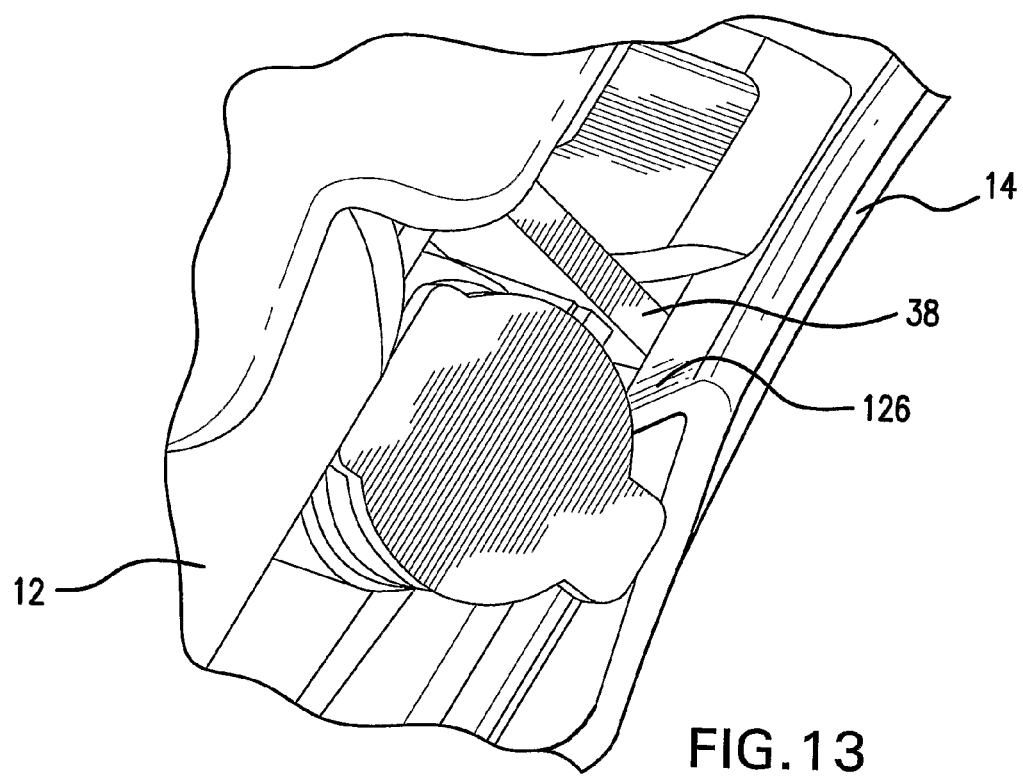
FIG. 13 depicts the inward protruding fin of a shield of the present invention passing over a properly inserted spike.

Shield body 80 also supports an inwardly-projecting fin 126. Fin 126 is positioned to slide along slots 74 and 76 of base 12. Fin 126 projects into spike receptacle 50 such that when spike 16 is properly seated therein, fin 126 will clear past planar base 38, as shown in FIG. 13. However, if spike 16 is not properly inserted into receptacle 50, fin 126 will catch on planar base 38 of spike 16 and thereby prevent shield 14 from being further retracted. Thus, fin 126 provides an antimalassembly feature to holder 10. Slots 74 and 76 are sized to allow fin 126 to move therealong as shield 14 moves between the extended and retracted positions.

With additional reference to FIGS. 14 and 15, deflectable tabs 92, 94, and 96 of shield 14 are positioned in overlying registry with grooves 66, 68, and 70 of base 12, respectively. With shield 14 in the extended, or raised, position, the teeth 106, 108, and 110 of tabs 92, 94, and 96, respectively are positioned above the detent 72 in each of grooves 66, 68, and 70. The grooves and teeth of components 12 and 14 allow shield 14 to be telescopically moved between an extended position, where a cap 202 may be received in end 84 while still spaced from spike 16, to a retracted position, where septum 204 of cap 202 will be pierced by spike 16. Cap 202 of container 200, once inserted and retained by detents 112, 114, and 116, does not move relative to the shield 14 as it telescopically moves between the extended and retracted position. Detents 112, 114, and 116 are formed to still allow, however, easy removal of the container cap from the shield 14 when desired. Between bottle changes spike 16 is protected from contamination by shield 14 extending perimetrically about it. As seen in FIGS. 1-4, the stand provides a second holding arm 148 into which a portion of the conduit extending between the spike and the luer lock may be inserted and retained.

Figure 10:
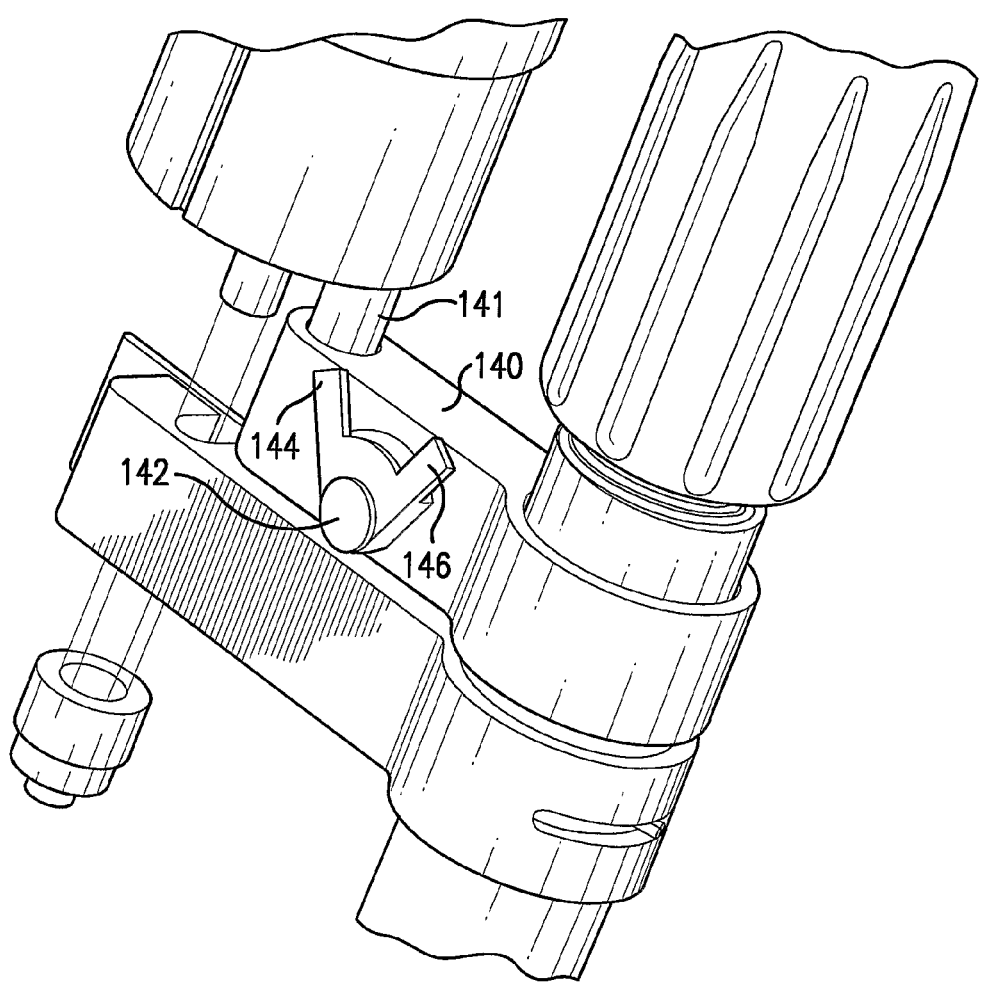
FIG. 10 depicts a bottle opener mounted to a holder arm for the bottle holder of the present invention.
Figure 11:
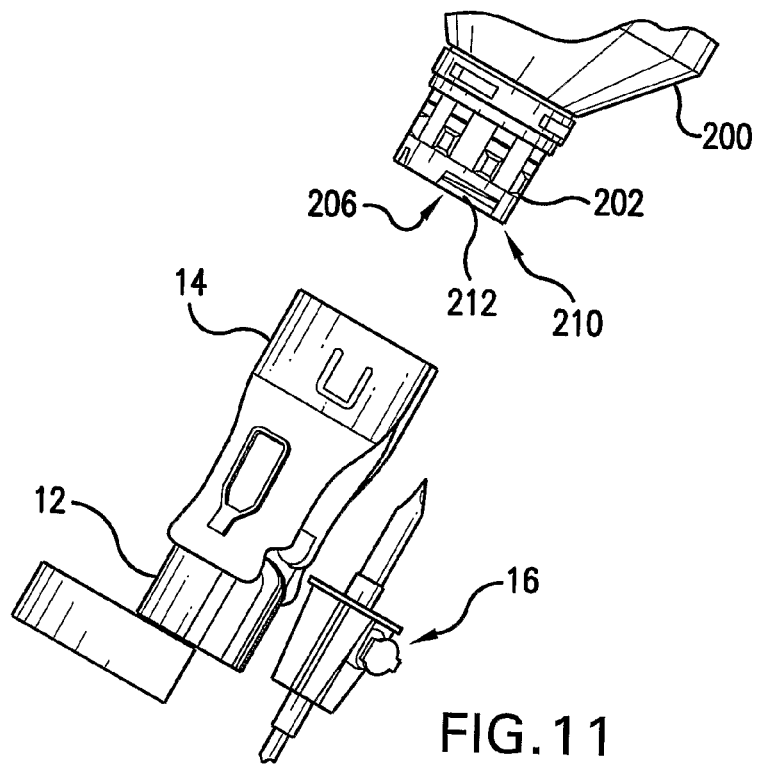
FIG. 11 depicts a bottle holder of the present invention showing spike approaching the spike receptacle and a bottle approaching the bottle receptacle.

With reference to FIG. 10, a bottle opener 142 with engagement twigs 144 and 146 may be provided on mounting arm 140. Twigs 144 and 146 are spaced from mounting arm 140 so that the pull tab of the bottle cap may be hung on the twigs of opener 142. When fully home on the twigs, the bottle is leveraged downwards, and the top is broken off, exposing the septum.

Figure 12:
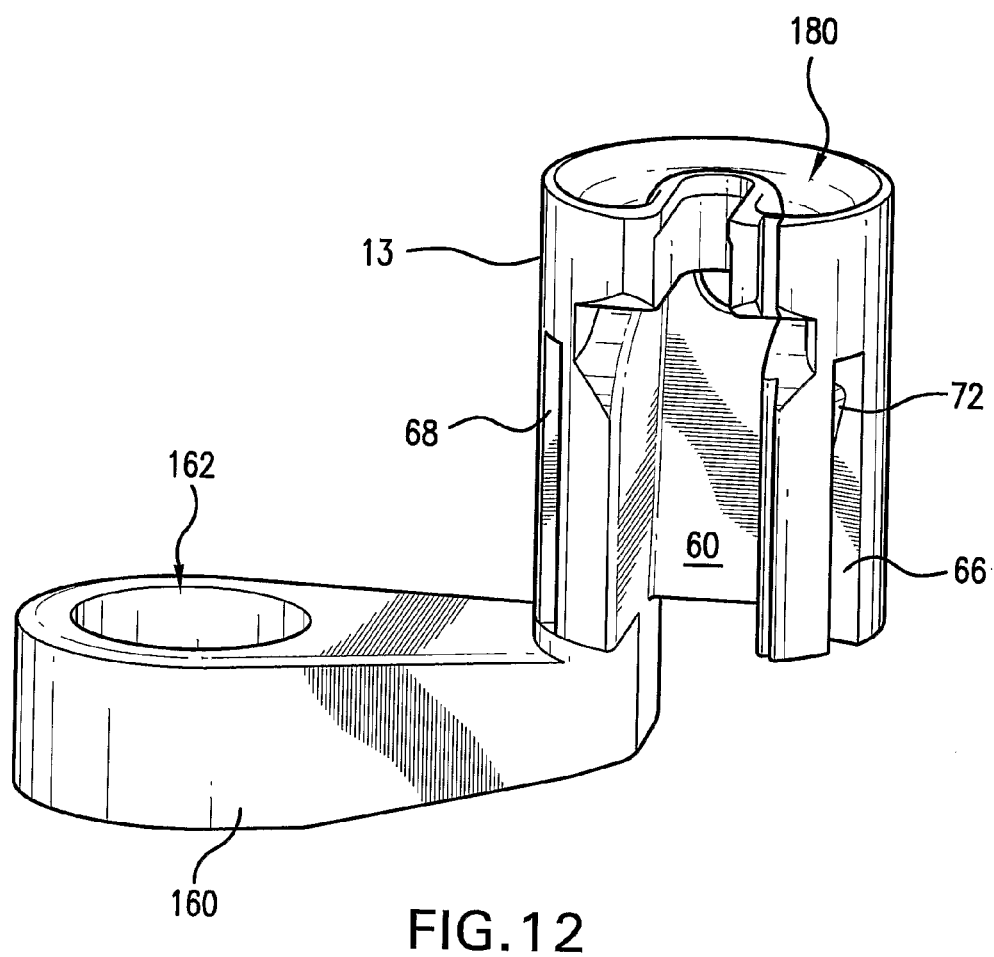
FIG. 12 depicts an alternate base of the present invention having an integral holder arm for mounting.

Referring now to FIG. 12, an alternate embodiment for base 12 provides base body 13 and an integrated mounting arm 160 which defines a through passage 162 for mounting pole 15. A spill channel 180 may be defined by the upper surface of base body 13 for catching any liquid from bottle 200 which may leak during spike insertion or withdrawal through septum 204. It is further contemplated that spill channel 180 may be provided with an absorbent material for also absorbing any spilled product. Desirably, mounting arms 140 and 160 are able to rotate about pole 15 so as to ease operator positioning of holder 10.

Figure 16:
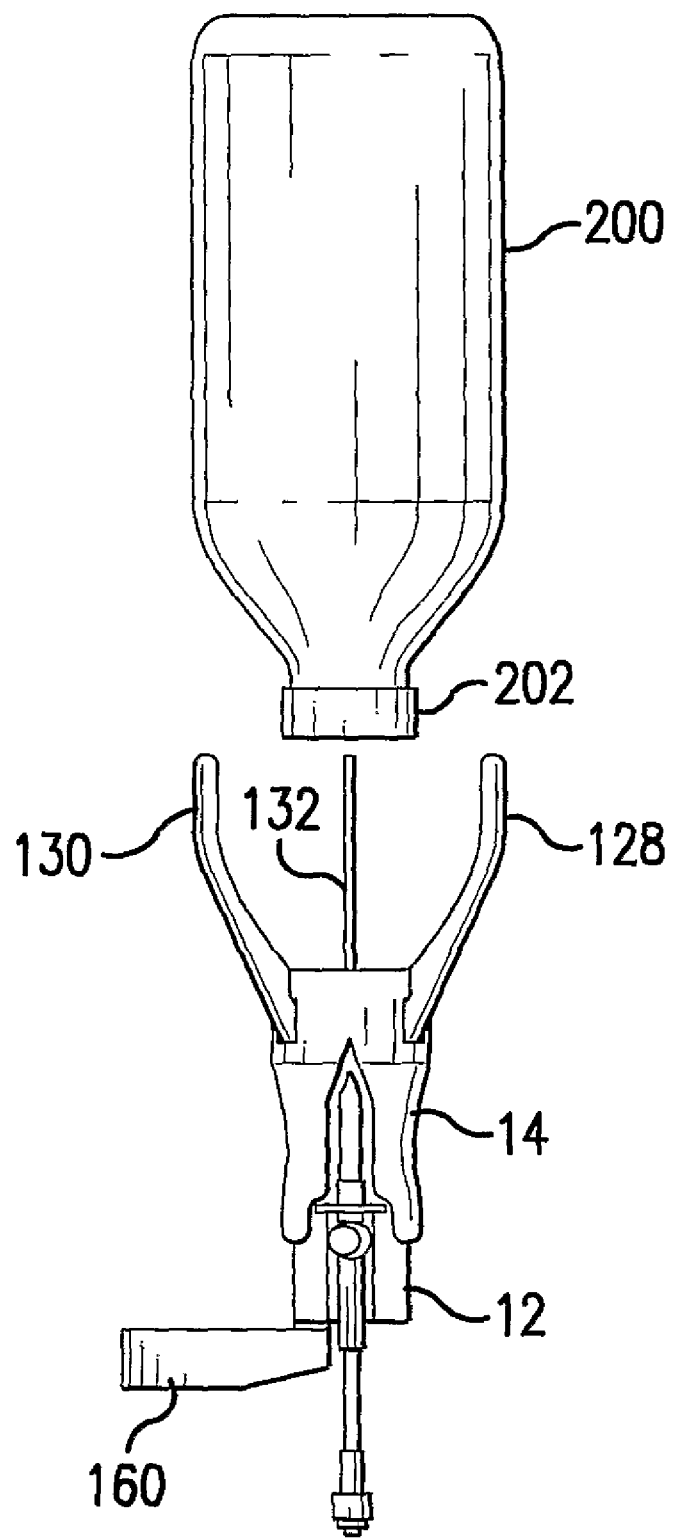
FIG. 16 depicts another embodiment of the present invention incorporating elongate arms for better securing a bottle in the shield.
Figure 19:
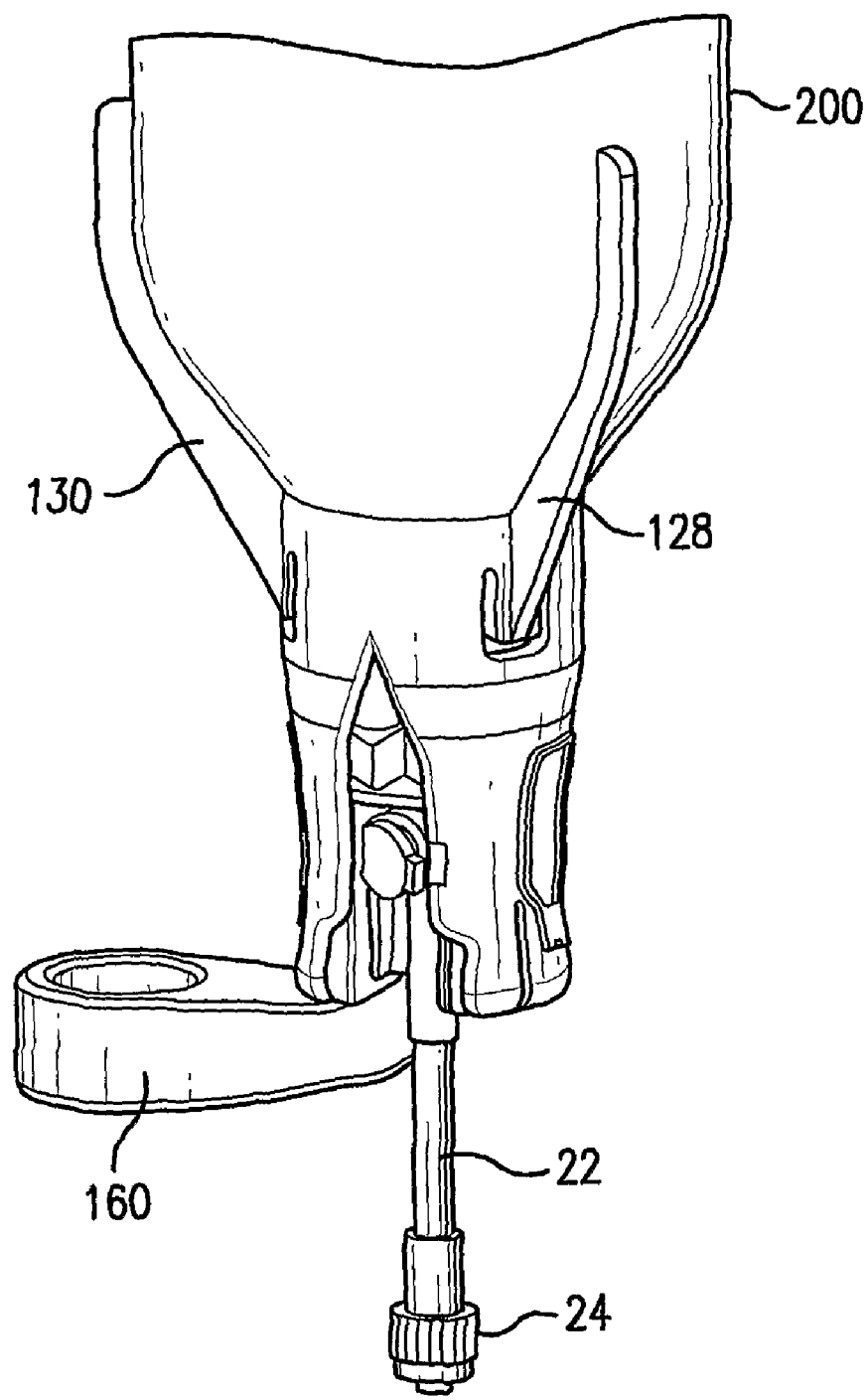
FIG. 19 depicts a bottle held by a holder of FIG. 16.

As shown in FIGS. 16 and 19, bottle holder 10 may also include elongate cantilever arms 128, 130, 132 extending from open end 84 of shield 14 so as to hold bottle 200 therebetween. Arms 128, 130, and 132 provide additional stability to a bottle inserted into bottle receptacle 52. Desirably, arms 128, 130, 132 are supported by, and connected to bottle holder 10, at deflectable detents 112, 114, and 116. FIGS. 17 and 18 depict cross-sectional views of holder 10 in both the extended, or raised, and retracted, or lowered, positions.

In operation, once spike 16 is inserted into base 12 a bottle 200 may be inserted into the fully-extended shield 14. As bottle 200 is inserted into receptacle 52, bottle detents 112, 114, and 118 will first deflect so that bottle is held in place in open end 84 of shield 14. The septum 204 of container cap 202 is centered over spike 16. Then as additional downward force is applied, each tooth 106, 108, and 1120 of deflectable tabs 92, 94, and 96 will ride over the detents 72 of base 12 so that shield 14 can slide linearly slide down grooves 92, 94, and 96, respectively. As bottle 200 is brought down with shield 14, septum 204 of bottle cap 206 comes down onto spike 16 which thus pierces septum 204. Contact between base 12 and annular rim 124 of shield 14 halts continued relative movement between base 12 and shield 14. Spike 16 will have penetrated into bottle 200 to allow fluid flow therefrom. Spike vent 32 may be opened to further assist fluid flow out conduit 22. Once the contents from bottle 200 are dispensed, shield 14 may be extended back up so as to remove bottle 200 from spike 16. Continued raising of bottle 200 will lift it from shield 14, allowing a subsequent bottle to be inserted if so desired.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A holding device for a container having a cap with a septum to be pierced by a spike, said holding device comprising:
    A base comprising an elongate base body having opposed first and second ends and an elongate body extending therebetween, said base body defining an elongate open spike cavity extending between opposing ends thereof, said spike cavity receiving an elongate spike therein so that a free end of the spike extends beyond said base body from said spike cavity; and
    A shield comprising first and second opposed open ends and an elongate cylindrical wall extending therebetween, said cylindrical wall defining a transversely-opening spike receptacle through which the distal end of the spike may pass while being inserted into or withdrawn from said spike cavity of said base, said cylindrical wall further defining a bottle receptacle for receiving the cap and the septum of the container, wherein said spike receptacle is in fluid communication with said bottle receptacle;
    Wherein said shield is telescopically mounted over said base so as to be movable between a first position wherein the spike is clear of the container cap and a second position wherein the spike pierces through the septum of the container cap.

2. The holding device of claim 1, wherein said spike cavity of said base further opens along the length of said base body.

3. The holding device of claim 2, wherein said base further comprises at least one retaining clip for engaging the spike when inserted into said spike cavity.

4. The holding device of claim 1, wherein said wall of said shield further comprises a frustoconical wall extending between said bottle receptacle and the end about said base.

5. The holding device of claim 4, wherein said frustoconical wall further comprises at least one deflectable tab for engaging the cap of the container.

6. The holding device of claim 5 wherein said frustoconical wall further comprises three deflectable tabs for engaging the cap of the container.

7. The holding device of claim 5, further comprising a plurality of cantilever arms each extending from a respective said deflectable tab of said shield.

8. The holding device of claim 1, wherein said base further comprises a tab for engaging a vent cover seated on a vent on the spike so that as said spike is inserted into said spike cavity, said tab unseats the vent cover from the vent.

9. The holding device of claim 8, wherein said tab is removable from said base so as to allow the spike to be inserted into the spike cavity without unseating the vent cover.

10. The holding device of claim 1, wherein said shield supports an inwardly-directed fin which will engage an improperly inserted spike and prevent said shield from being sufficiently retracted so as to allow the spike to pierce the septum of the container.

11. The holding device of claim 1, further comprising a mounting arm extending between a first elongate pole and a pin on which said base is attached.

12. The holding device of claim 11, further comprising engagement twigs affixed to said mounting arm for engaging a removable tab on the container.

13. The holding device of claim 1, further comprising an inwardly-projecting annular rim extending about the interior surface of said shield, said rim providing a hard stop for retraction of said shield towards said base.

14. The holding device of claim 10, wherein said base defines a slot for said fin to pass through as said shield is moved.

15. The holding device of claim 1, further comprising a mounting unit integral to said base.

16. The holding device of claim 1, further comprising a plurality of cantilever arms extending from said holder so as to hold an inserted bottle therebetween.

17. The holding device of claim 1, further comprising cooperating grooves and teeth on said base and shield for providing linear movement of said shield between said extended and retracted positions.

18. The holding device of claim 17, wherein said shield deflectably supports a plurality of teeth for engaging a respective groove defined by said base.

19. The holding device of claim 18, wherein said grooves defined by said base each support a fixed detent for engaging a respective tooth of said shield.

* * * * *